United States Patent
Hsieh et al.

(10) Patent No.: US 11,389,507 B2
(45) Date of Patent: Jul. 19, 2022

(54) **USE OF INTERLEUKIN-4-INDUCING PRINCIPLE OF *SCHISTOSOMA MANSONI* EGGS FOR TREATING PAIN, INTERSTITIAL CYSTITIS AND/OR OVERACTIVE BLADDER**

(71) Applicant: BIOMEDICAL RESEARCH INSTITUTE, Rockville, MD (US)

(72) Inventors: Michael Hsieh, Bethesda, MD (US); Loc Huu Le, Amarillo, TX (US); Evaristus Chibunna Mbanefo, Montgomery Village, MD (US)

(73) Assignee: BIOMEDICAL RESEARCH INSTITUTE, Rockville, MD (US)

( * ) Notice: Subject to any disclaimer, the term of this patent is extended or adjusted under 35 U.S.C. 154(b) by 0 days.

(21) Appl. No.: 16/623,230

(22) PCT Filed: Jun. 14, 2018

(86) PCT No.: PCT/US2018/037528
§ 371 (c)(1),
(2) Date: Dec. 16, 2019

(87) PCT Pub. No.: WO2018/232112
PCT Pub. Date: Dec. 20, 2018

(65) Prior Publication Data
US 2020/0164030 A1 May 28, 2020

Related U.S. Application Data

(60) Provisional application No. 62/519,851, filed on Jun. 14, 2017, provisional application No. 62/519,855, filed on Jun. 14, 2017, provisional application No. 62/519,860, filed on Jun. 14, 2017.

(51) Int. Cl.
*A61K 38/17* (2006.01)
*A61K 9/00* (2006.01)

(52) U.S. Cl.
CPC ........ *A61K 38/1767* (2013.01); *A61K 9/0019* (2013.01); *A61K 9/0021* (2013.01); *A61K 9/0031* (2013.01); *A61K 9/0043* (2013.01); *A61K 9/0053* (2013.01)

(58) Field of Classification Search
CPC .................................................. A61K 38/1767
See application file for complete search history.

(56) References Cited

U.S. PATENT DOCUMENTS 7,601,812 B2 * 10/2009 Schramm ................ A61P 37/06
530/351

OTHER PUBLICATIONS

Singh et al. "The Severity of Experimental Autoimmune Cystitis Can be Ameliorated by Anti-CXCL10 Ab Treatment." PLoS ONE 8(11): e79751 (2013) (Year: 2013).*

Oguchi et al. "Effect of herpes simplex virus vector-mediated interleukin-4 gene therapy on bladder overactivity and nociception". Gene Therapy (2013) 20, 194-200. (Year: 2013).*
Fu et al. "A Novel Mouse Model of Schistosoma haematobium Egg-Induced Immunopathology". PLoS Pathog 8(3): e1002605 (2012) (Year: 2012).*
Young et al. "Whole-genome sequence of Schistosoma haematobium" Nature Genetics vol. 44, pp. 221-225 (2012) (Year: 2012).*
Shargel et al. Chapter 8. Multiple-Dosage Regimens, in Applied Biopharmaceutics & Pharmacokinetics (Sixth Edition) [online] [2014 archived version accessed from web.archive.org/web/20140713081259/https://accesspharmacy.mhmedical.com/content.aspx?bookid=513&sectionid=41488026]. (Year: 2014).*
Lee et al. "Is interstitial cystitis an allergic disorder?: A case of interstitial cystitis treated successfully with anti-IgE". International Journal of Urology (2006) 13, 631-634 (Year: 2006).*
Schramm et al. "Cutting Edge: IPSE/alpha-1, a Glycoprotein from Schistosoma mansoni Eggs, Induces IgE-Dependent, Antigen-Independent IL-4 Production by Murine Basophils In Vivo". J Immunol 2007; 178:6023-6027. (Year: 2007).*
Schmidt, R. "Dose-Finding Studies in Clinical Drug Development" Eur J Clin Pharmacol 1988 34: 15-19. (Year: 1988).*
White, P.F. "Clinical Uses of Intravenous Anesthetic and Analgesic Infusions". Anesthesia & Analgesia: Feb. 1989—vol. 68—Issue 2—p. 161-171. (Year: 1989).*
Pai et al. "Pharmacokinetics and Pharmacodynamics of Continuous Infusion Meropenem in Overweight, Obese, and Morbidly Obese Patients with Stable and Unstable Kidney Function: A Step Toward Dose Optimization for the Treatment of Severe Gram-Negative Bacterial . . . ". Clin Pharmacokinet (2015) 54:93 (Year: 2015).*
Fields et al. "Effect of Rapid Intravenous Infusion on Serum Concentrations of Amphotericin B". Applied Microbiology, Oct. 1971, p. 615-617. (Year: 1971).*
Animal Resources Centre. "Rat and Mice Weights" [online][2015 archived version accessed on Mar. 9, 2021 from web.archive.org/web/20150310183127/https://www.arc.wa.gov.au/?page_id=125](Year: 2015).*

(Continued)

*Primary Examiner* — Prema M Mertz
(74) *Attorney, Agent, or Firm* — Edell, Shapiro & Finnan, LLC

(57) ABSTRACT

Methods are provided for the prevention and/or treatment of pain, interstitial cystitis and/or overactive bladder in a subject using an IPSE protein, such as H03 H-IPSE, H06 H-IPSE, M-IPSE or other IPSE homologs, variants, mutants or mimics. The IPSE protein can be administered prior to, contemporaneously with, and/or after the subject develops pain, interstitial cystitis and/or overactive bladder. Pharmaceutical compositions also are provided that contain one or more IPSE proteins in a pharmaceutically acceptable carrier, excipient or diluent.

14 Claims, 14 Drawing Sheets

Specification includes a Sequence Listing.

(56) References Cited

OTHER PUBLICATIONS

"MS3_10186 hypothetical protein" [online][accessed from schistodb.net/schisto/app/record/gene/MS3_10186#BlatAlignmentsGbrowseUrl on Mar. 9, 2021] (Year: 2015).*

"MS3_11169 hypothetical protein" [online][accessed from schistodb.net/schisto/app/record/gene/MS3_11169#GeneModelGbrowseUrl on Mar. 9, 2021] (Year: 2015).*

* cited by examiner

SEQUENCE LISTING

```
<160> NUMBER OF SEQ ID NOS: 8

<210> SEQ ID NO 1
<211> LENGTH: 7
<212> TYPE: PRT
<213> ORGANISM: Schistosoma mansoni

<400> SEQUENCE: 1

Pro Lys Arg Arg Arg Thr Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Lys Ala Ala Ala Thr Tyr
1               5

<210> SEQ ID NO 3
<211> LENGTH: 7
<212> TYPE: PRT
<213> ORGANISM: Unknown
<220> FEATURE:
<223> OTHER INFORMATION: Description of Unknown:
      H-IPSE nuclear localization sequence

<400> SEQUENCE: 3

Ser Lys Arg Arg Arg Lys Tyr
1               5
```

```
<210> SEQ ID NO 4
<211> LENGTH: 7
<212> TYPE: PRT
<213> ORGANISM: Schistosoma haematobium

<400> SEQUENCE: 4

Ser Lys Arg Gly Arg Lys Tyr
1               5

<210> SEQ ID NO 5
<211> LENGTH: 5
<212> TYPE: PRT
<213> ORGANISM: Unknown
<220> FEATURE:
<223> OTHER INFORMATION: Description of Unknown:
      NLS core sequence

<400> SEQUENCE: 5

Lys Arg Arg Arg Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ala Ala Gly Ala Ala Tyr
1               5

<210> SEQ ID NO 7
<211> LENGTH: 134
<212> TYPE: PRT
<213> ORGANISM: Schistosoma haematobium

<400> SEQUENCE: 7

Met Phe Leu Ile Ala Leu Leu Ser Tyr Thr Leu Ile Asn Gln Leu Val
1               5                   10                  15

Ile Thr Lys Ser Asp Ser Cys Lys Tyr Cys Leu Arg Leu Tyr Asp Gly
                20                  25                  30

Lys Tyr Lys Ser Gly Ser Tyr Ile Glu Val Tyr Lys Ser Val Gly Ser
            35                  40                  45

Leu Ser Pro Pro Trp Ile Pro Gly Ser Val Cys Val Pro Leu Ile His
    50                  55                  60

Asn Ser Thr Gly Gln Pro Pro Tyr Trp Arg Ile Tyr Glu Asp Val Asn
65                  70                  75                  80

Tyr Ser Gly Ala Asn Thr Ala Val Gly His Gly Ala Cys Ile Asp Asp
                85                  90                  95

Phe Met Lys Ser Gly Leu Arg Arg Ile Ser Ser Ile Gln Lys Cys Val
            100                 105                 110

Tyr Gly Glu Asn Gly Met Val Gln Cys Ile Ser Glu Ser Lys Arg Gly
        115                 120                 125

Arg Lys Tyr Cys Arg Tyr
        130

<210> SEQ ID NO 8
<211> LENGTH: 134
<212> TYPE: PRT
```

```
<213> ORGANISM: Schistosoma mansoni

<400> SEQUENCE: 8

Met Phe Leu Ile Ala Val Leu Ser Tyr Thr Leu Ile Ser Gln Leu Gly
1               5                   10                  15

Ile Thr Thr Ser Asp Ser Cys Lys Tyr Cys Leu Gln Leu Tyr Asp Glu
            20                  25                  30

Thr Tyr Glu Arg Gly Ser Tyr Ile Glu Val Tyr Lys Ser Val Gly Ser
        35                  40                  45

Leu Ser Pro Pro Trp Thr Pro Gly Ser Val Cys Val Pro Phe Val Asn
    50                  55                  60

Asp Thr Lys Arg Glu Arg Pro Tyr Trp Tyr Leu Phe Asp Asn Val Asn
65                  70                  75                  80

Tyr Thr Gly Arg Ile Thr Gly Leu Gly His Gly Thr Cys Ile Asp Asp
                85                  90                  95

Phe Thr Lys Ser Gly Phe Lys Gly Ile Ser Ser Ile Lys Arg Cys Ile
            100                 105                 110

Gln Lys Asp Gly Lys Val Glu Cys Ile Asn Gln Pro Lys Arg Arg
        115                 120                 125

Arg Thr Tyr Cys Arg Phe
130
```

USE OF INTERLEUKIN-4-INDUCING PRINCIPLE OF *SCHISTOSOMA MANSONI* EGGS FOR TREATING PAIN, INTERSTITIAL CYSTITIS AND/OR OVERACTIVE BLADDER

CROSS REFERENCE TO RELATED APPLICATIONS

This application is a National Phase application of International Application No. PCT/US2018/037528, filed on Jun. 14, 2018, which claims priority to provisional applications 62/519,851, filed Jun. 14, 2017, 62/519,855, filed Jun. 14, 2017, and 62/519,860, filed Jun. 14, 2017, the contents of each of which are hereby incorporated by reference in their entireties.

The instant application contains a Sequence Listing which has been submitted electronically in ASCII format and is hereby incorporated by reference in its entirety. Said ASCII copy, created on Aug. 24, 2020, is named 3965_0002C_SL.txt and is 3,999 bytes in size.

FIELD OF THE INVENTION

Methods of treating interstitial cystitis, pain, and overactive bladder using the Interleukin-4-Inducing Principle of *Schistosoma mansoni* eggs (IPSE) are provided. Therapeutically useful derivatives, homologs, analogs, and mimics of IPSE for treating interstitial cystitis, pain, and overactive bladder are also provided.

BACKGROUND OF THE INVENTION

Interstitial cystitis/bladder pain syndromes deeply impact affected individuals. A set of symptoms that features bladder hypersensitivity encompasses interstitial cystitis. The International Continence Society has previously defined interstitial cystitis/painful bladder syndrome as " . . . the complaint of suprapubic pain related to bladder filling, accompanied by other symptoms such as increased daytime and nighttime frequency, in the absence of proven urinary infection or other obvious pathology". Among men, it has been estimated that the weighted prevalence of interstitial cystitis ranges between 1.9-4.2%, or up to 2.1 million affected individuals, depending on the diagnostic definition used. Two other studies have made similar calculations, with prevalence among men in a managed care setting of up to 4.6%. These and other studies have reported a wide range of possible prevalence for interstitial cystitis among women (like men, depending on study population and diagnostic definitions), from as low as 0.045% to as high as 30%. Although the exact definition and prevalence of interstitial cystitis/bladder pain syndromes continues to be debated, there is agreement that this constellation of syndromes and commonly associated comorbidities cause significant pain and suffering.

Overactive bladder syndrome affects a large proportion of all humans. The International Continence Society has defined overactive bladder syndrome as being characterized by urinary urgency, with or without urgency urinary incontinence, usually with increased daytime frequency and nocturia, if there is no proven infection or other obvious pathology. Overactive bladder syndrome has been estimated to have a prevalence of 16-17% among all U.S. men and women. This syndrome increases in prevalence with age; some have estimated a rate of >40% in the over 40 age group, across both men and women. Accordingly, others have calculated that nearly 30 million people aged 40 or older have overactive bladder syndrome. One or more studies have shown that overactive bladder syndrome is associated with a significant negative quality-of-life impact. Thus, overactive bladder syndrome is a highly prevalent set of symptoms associated with chronic sequelae. Novel non-opioid analgesics are needed. In 2015, approximately 33,000 people in the U.S. died from opioid abuse, nearly equaling car crash fatalities. Heroin-related deaths alone surpassed gun homicides. Much of the opioid epidemic has resulted from addiction to opioids originally prescribed to treat pain. The reliance upon opioids for analgesia is largely driven by the lack of good non-opioid alternatives. Analgesics such as aspirin, acetaminophen, and non-steroidal anti-inflammatory drugs (NSAIDs) have limited efficacy and maximum safe daily doses. Nerve blocks and corticosteroid injections are invasive and painful. Topical therapy (i.e., capsaicin, NSAIDs) may not successfully target deeper pain. Anticonvulsants, muscle relaxants, and antidepressants can result in significant side effects. Non-medical pain management approaches, i.e., massage, acupuncture, yoga, and relaxation techniques, are rarely sufficient as monotherapy. Thus, there is a major need for new non-opioid analgesics. Inflammation has been implicated in many types of pain treated with opioids, which explains the limited success of NSAIDs and corticosteroids. Despite the importance of inflammation in pain, there are few therapeutic agents that target inflammation.

Overactive bladder syndrome affects a large proportion of all humans. The International Continence Society has defined overactive bladder syndrome as being characterized by urinary urgency, with or without urgency urinary incontinence, usually with increased daytime frequency and nocturia, if there is no proven infection or other obvious pathology. Overactive bladder syndrome has been estimated to have a prevalence of 16-17% among all U.S. men and women. This syndrome increases in prevalence with age; some have estimated a rate of >40% in the over 40 age group, across both men and women. Accordingly, others have calculated that nearly 30 million people aged 40 or older have overactive bladder syndrome. One or more studies have shown that overactive bladder syndrome is associated with a significant negative quality-of-life impact. Thus, overactive bladder syndrome is a highly prevalent set of symptoms associated with chronic sequelae.

SUMMARY OF THE INVENTION

Methods of preventing or treating interstitial cystitis, pain and/or overactive bladder in a subject are provided, by administering to the subject an effective dose of an Interleukin-4-Inducing Principle of *Schistosoma mansoni* eggs (IPSE) protein. The IPSE protein can be, for example, H03 H-IPSE, H06 H-IPSE and/or M-IPSE or its derivatives, homologs, analogs, mutants, variants, and mimics. The effective dose of the IPSE protein may be administered prior to or contemporaneously with establishment of interstitial cystitis, exposure to painful stimuli, and/or developing or having overactive bladder. One or more further doses of an IPSE protein may be given after establishment of interstitial cystitis, exposure to the one or more painful stimuli or development of overactive bladder. The protein can be administered, for example, intravenously or subcutaneously. Dosage of the protein can be 0.1-20 mg/kg, but advantageously is at least 1 mg/kg.

In an embodiment, a single dose of H03 H-IPSE is given intravenously to treat interstitial cystitis, pain and/or overactive bladder. In another embodiment, a single dose of H06

H-IPSE is given intravenously to treat interstitial cystitis, pain and/or overactive bladder. In a still further embodiment, a single dose of M-IPSE is given as therapy for established interstitial cystitis, pain and/or overactive bladder. In yet another preferred aspect, non-H03 homologs or non-H06 homologs of H-IPSE are given therapeutically as a single dose to treat established interstitial cystitis, pain and/or overactive bladder.

In other aspects, mutant forms of H-IPSE (H03, H06, or other homologs) or M-IPSE, generated, for example, using error-prone PCR or targeted mutagenesis, are given intravenously as a single dose to treat established interstitial cystitis pain and/or overactive bladder.

IPSE homologs or mimics are suspended in a solution of sterile water for injection or bacteriostatic water for injection. In another aspect, IPSE homolog(s) or mimic(s) are prepared as powders ready for resuspension in sterile water for injection or bacteriostatic water for injection.

In yet another aspect, IPSE homologs or mimics are administered by subcutaneous injection.

In further aspects, treatment may be repeated, i.e., the IPSE homolog(s) or mimic(s) are administered more than once. One aspect of this procedure is that the IPSE homolog(s) or mimic(s) are given before and during interstitial cystitis, pain and/or overactive bladder. In another preferred embodiment, all doses of IPSE homolog(s) or mimic(s) are given before interstitial cystitis, pain and/or overactive bladder Finally, in another aspect, all doses of IPSE homolog(s) or mimic(s) are given after interstitial cystitis, pain and/or overactive bladder establishment or onset.

Methods hence are provided herein for using IPSE homologs or mimics to prevent or treat interstitial cystitis, pain and/or overactive bladder.

DETAILED DESCRIPTION

Figure 1:
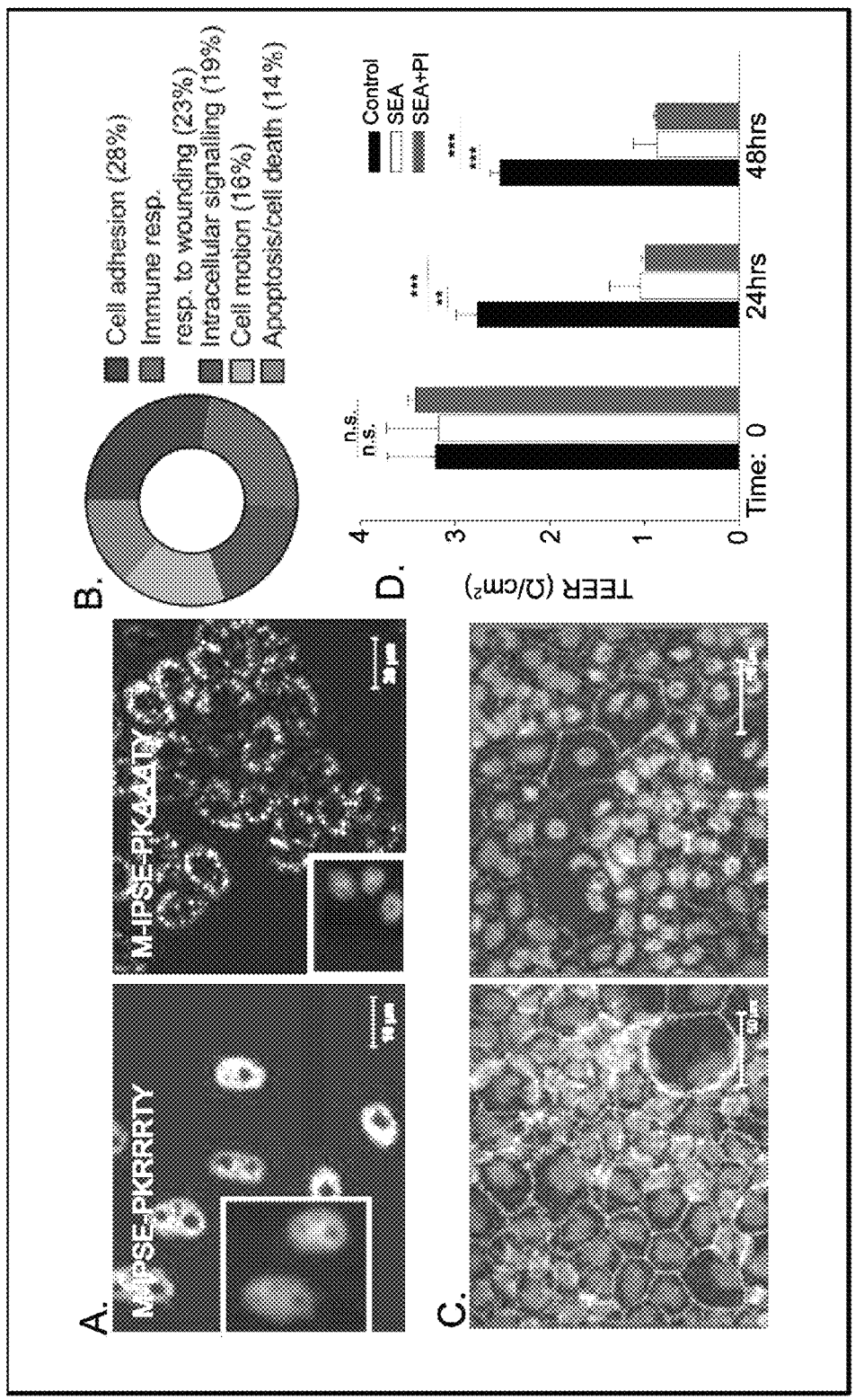
FIG. 1 shows that exogenously applied M-IPSE entered mammalian cells, translocated into the cell nucleus, and modulated gene expression and epithelial integrity: Panel A. shows uptake and subcellular localization of exogenously added M-IPSE. CHO cells were incubated with recombinant IPSE for 30 min at 37° C. and stained with a monoclonal anti-IPSE primary antibody and an Alexa 594-labeled secondary antibody (red). Wildtype 'PKRRRTY' IPSE ("PKRRRTY" disclosed as SEQ ID NO: 1) translocated to the nucleus in the presence of an intact nuclear localization sequence [NLS] (A), but not an IPSE 'PKAAATY' NLS triple mutant ("PKAAATY" disclosed as SEQ ID NO: 2), showing uptake but loss of nuclear translocation (B). Panel B.) shows functional annotation clustering of genes upregulated in monocyte-derived dendritic cells (MDDCs) incubated with recombinant IPSE (Gene Ontology term GOTERM_BP_FAT in the category of biological processes filtered by DAVID specific algorithm FAT). Panel C.) shows the effect of long term (48 hr) incubation of polarised Caco-2 cells with schistosome egg antigen (SEA) (A: no SEA; B: with SEA), containing IPSE as a major component. Staining was with a monoclonal antibody to ZO-1 (red). Nuclei were stained in blue with Hoechst dye. Note that ZO-1 has an intracellular location, suggesting that the apparent reduction was not caused by proteases contained in SEA. Panel D) shows changes in trans-endothelial electrical resistance (TEER) at 0, 24 and 48 hours induced by SEA containing IPSE (light grey bars) compared to incubation with medium (dark grey bars), consistent with increased leakiness of the tight junctions, independently of protease activity. P values are from paired Student's t-test.

Methods are provided for the prevention and/or treatment of interstitial cystitis, pain, and/or overactive bladder in a subject, such as a human patient, by administration of one or more effective doses of an IPSE protein, its derivatives, homologs, analogs, mutants, variants, and mimics as analgesics. The IPSE protein can be administered prior to, contemporaneously with, and/or after the subject develops interstitial cystitis, is exposed to a painful stimulus and/or develops overactive bladder. The IPSE protein can be administered intravenously, for example, or subcutaneously or any other suitable route of administration.

Pharmaceutical compositions also are provided that contain one or more IPSE proteins in a pharmaceutically acceptable carrier, excipient or diluent. The composition can be provided in a ready to use format or can be provided in a dry form that can be suspended or dissolved in a carrier, diluent or excipient just prior to administration.

Administration may be repeated, i.e., the IPSE protein can be administered 2, 3, 4, or more times, for example before and during experiencing interstitial cystitis, exposure to a painful stimulus of experiencing pain, overactive bladder. In one embodiment, all doses of the IPSE protein are given prior to experiencing interstitial cystitis, overactive bladder or being exposed to a painful stimulus. In another embodiment, all doses of IPSE homolog(s) or mimic(s) are administered after development of interstitial cystitis, overactive bladder or exposure to a painful stimulus.

Immune and non-immune modulation of bladder biology is a promising therapeutic approach for bladder hypersensitivity. Immune and non-immune modulation of the bladder may be a new management approach for bladder hypersensitivity and/or overactive bladder. For example, blocking CCL2-CCR2 interactions in bladder nerves and dorsal root ganglia lowers pain in rodent cystitis models. Recombinant IL-4 lessens ifosfamide-induced cystitis in mice almost as well as Mesna, the standard of care. Virally delivered IL-4 induces bladder and dorsal root ganglia expression of IL-4 and decreases bladder pain and overactivity caused by resiniferatoxin, a TRPV1 pain receptor ligand. Yet, giving intravenous IL-4 to patients can result in fever, headache, capillary leak syndrome, transaminitis, and elevated hepatic alkaline phosphatase, suggesting that this cytokine may be a suboptimal therapeutic for bladder hypersensitivity.

The TRPV1 pain receptor may be a good specific target for immune and non-immune modulation of bladder hypersensitivity and/or overactive bladder. Independent of IL-4's suitability, or lack thereof, as a therapeutic for bladder hypersensitivity and/or overactive bladder, it is apparent that TRPV1 expression in bladder-innervating afferent neurons may play a role in interstitial cystitis as well as interstitial cystitis/bladder pain and overactivity syndromes. Interestingly, pain induces CCL2 expression in dorsal root ganglia, and specifically in TRPV1-expressing neurons. CCL2 itself upregulates TRPV1 receptors in dorsal root ganglia. Another chemokine, CCL3, sensitizes TRPV1 receptors. Thus, therapeutic modification of CCL2, CCL3, and other molecules which regulate TRPV1 activity may be a promising avenue of research for bladder hypersensitivity and/or overactive bladder.

Chemokines have also been implicated in cyclophosphamide-induced bladder pain and may be a therapeutic target. Others have reported that CCL2 and its receptor, CCR2, is upregulated in the bladder urothelium and bladder-afferent dorsal root ganglia of cyclophosphamide-exposed rats. Moreover, inhibiting CCR2 pharmacologically reduced voiding frequency and enhanced bladder capacity and void volume in these rats. CCR2 blockade, at the level of the urinary bladder, reduced referred somatic sensitivity of the hindpaw and pelvic region in cyclophosphamide-exposed rats, as determined with von Frey filament testing. In another publication, CCL5 was reported to be upregulated in the cyclophosphamide-exposed rat bladder. Hence, chemokines appear to play an important role in chemotherapy-induced bladder hypersensitivity, and may be a promising therapeutic target.

IPSE Proteins

Therapy using whole parasites and parasite products is emerging as a novel approach to treat one or more diseases. Parasite-derived molecules hold promise as non-opioid, anti-inflammatory analgesics. Parasites have closely co-evolved with humans, and in the process have evolved the ability to produce molecules which modulate host inflammation to prevent parasite death. This observation has led to "helminth therapy", including administration of helminth eggs to patients with inflammatory bowel disease to decrease disease flares and symptoms. A more elegant approach to helminth therapy would be to generate recombinant parasite-derived proteins and administer these single proteins to patients based on known disease mechanisms.

The *Schistosoma haematobium* homolog of IPSE (Interleukin-4 inducing Principle from *Schistosoma mansoni* Eggs) is a molecule which may modulate *S. haematobium*-associated pain, interstitial cystitis and broader host bladder biology. Like ifosfamide, *S. haematobium* infection is associated with a form of interstitial cystitis, thought to be chiefly caused by inflammation induced by eggs deposited in the bladder wall. IPSE is an egg-secreted protein that modulates the host. *S. mansoni* IPSE (M-IPSE) is the most abundant *S. mansoni* egg-secreted protein. *S. mansoni* IPSE (referred to herein as M-IPSE) is a relatively small protein that is secreted as a homodimer, where each monomer of the mature secreted homodimer is only 114 amino acids long. M-IPSE is unique in that it has no homology with proteins outside the genus *Schistosoma*. M-IPSE is expressed in large amounts exclusively by the egg life stage of schistosomes, and even within that life stage is only produced by mature eggs. Chronic *S. haematobium* infection, but not *S. mansoni* infection, is associated with hematuria and increased risk of bladder cancer. Thus, the *S. haematobium* homolog of IPSE (H-IPSE) may be a species-specific molecule responsible for this schistosome's well-known ability to modulate interstitial cystitis and bladder cancer. M-IPSE has been described to have three distinct functions:

Immunoglobulin binding: M-IPSE is an IgE binding protein with some affinity for IgG, and has been shown to activate human basophils to secrete IL-4 in an IgE-dependent mechanism.

Nuclear localization: M-IPSE can translocate into the host cell nucleus and alter host gene expression (FIG. 1).

Chemokine binding: M-IPSE alters cellular composition of egg-associated granulomata binding and sequesters host chemokines.

Figure 2:
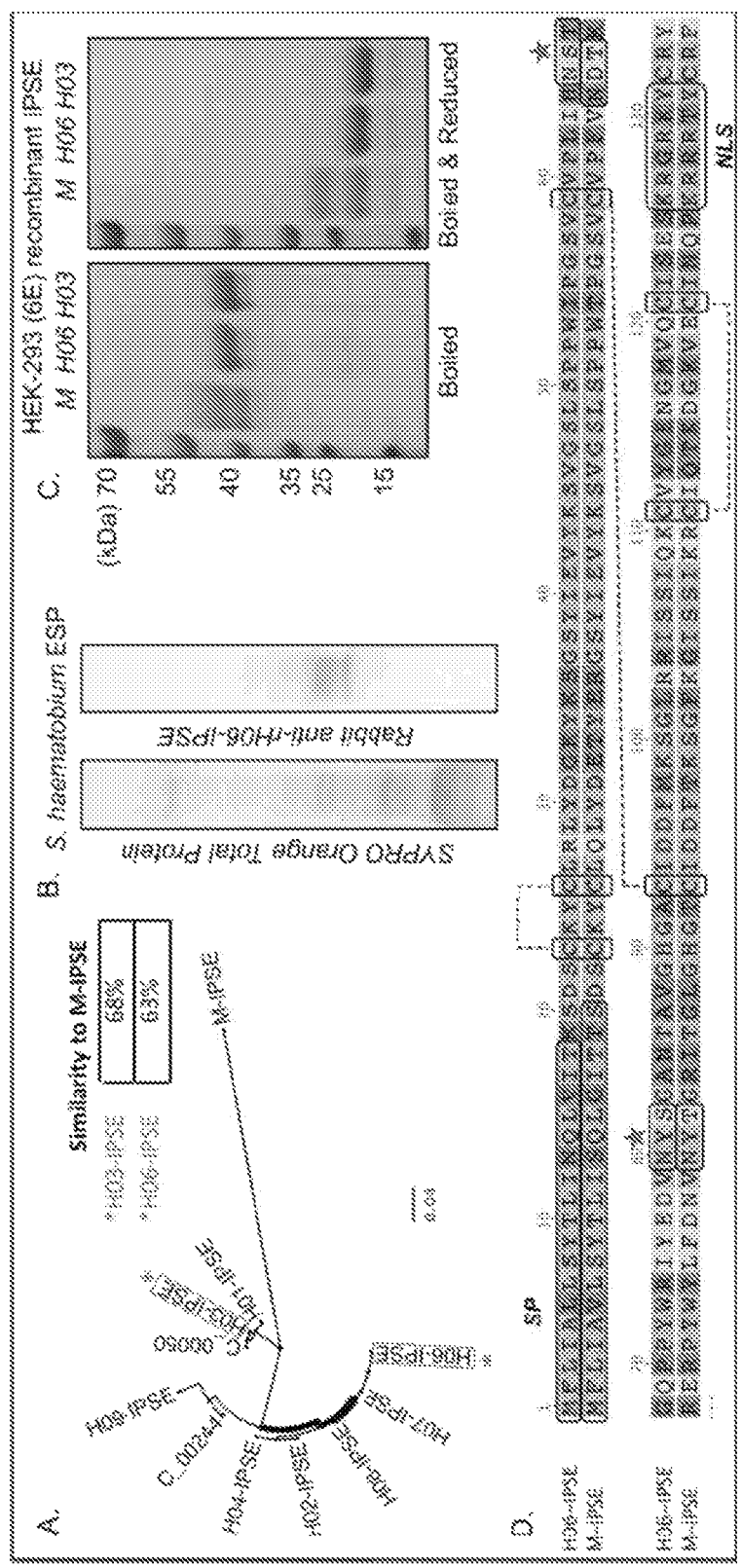
FIG. 2 shows identification and expression of multiple S. haematobium IPSE homologs. H-IPSE homologs were cloned using sequence data from the S. haematobium genome followed by rounds of 3' RACE cloning using conserved regions from original clones. The cloned H-IPSE variants ranged in similarity from M-IPSE, and corresponded well to predicted IPSE gene products C_00050 and C_00244 from parasite.wormbase.org. Panel (A.) shows a phylogenic tree representing distances by amino acid identity between H-IPSE variants and M-IPSE. H06 and H03 IPSE were selected as representatives of the two H-IPSE clusters observed, indicated by green asterisks. Panel (B.) shows recombinant bacterial H06-IPSE that was used to immunize rabbits to generate a polyclonal anti-IPSE antisera that detected IPSE in S. haematobium egg secreted proteins (right panel) Panel (C.) shows recombinant HEK-293-6E derived IPSE variants subjected to SDS-PAGE run at molecular weights consistent with the predicted molecular weight of the glycosylated homodimeric forms of M-IPSE described previously, and were reduced to monomeric species which correspond in size to the predicted glycoforms. Panel (D.) shows a comparison of H06-IPSE to M-IPSE, revealing 63% amino acid identity. The H-IPSE homologue also retained four important features: 1. A signal peptide (SP) 2. All cysteine residues involved in intra- and interchain disulfide bonds 3. Two N-linked glycosylation consensus motifs (blue stars) 4. A nuclear localization sequence (NLS)). Figure discloses SEQ ID NOS 7-8, respectively, in order of appearance.

To characterize *S. haematobium* IPSE (H-IPSE), the *S. haematobium* genome was examined and it was found that one or more H-IPSE gene sequences were predicted, suggesting that several polymorphisms/alleles of the H-IPSE gene exist. To address this possibility a 5' RACE strategy was used to expand one or more H-IPSE clones using forward primers in conserved 3' regions of predicted IPSE alleles. This analysis revealed that several IPSE variants were present in the parasite pool, which varied in similarity to M-IPSE sequences, and intriguingly which carried an R→G point mutation within the predicted nuclear localization sequence (FIG. 2d). Such variants have also been observed in S. mansoni studies. For example ESP3-6, a protein later recognized as an M-IPSE variant, is 97% homologous to the published M-IPSE sequence, but contains an R→L point mutation within the nuclear localization sequence (ESP3-6 GeneBank locus: AF527011). Positively charged amino acids in an NLS relate to its activity, thus such a replacement is expected to have an impact on the protein's ability to translocate to the nucleus, ranging from less efficient translocation to no translocation at all, depending on the exact position in the NLS, which defines its ability to interact with importin-alpha, and potentially also have an effect on DNA binding specificity.

The 3' RACE data were compared to the predicted IPSE transcripts from RNAseq data generated from S. haematobium eggs. Both the 3' RACE data, and the RNAseq data, identified two main H-IPSE variants (1898 and 1160 reads were mapped to these variants, indicating similar relative expression for both, FIG. 2a). Additional SNPs were also identified within these two variants. Despite sporadic point mutations in some variants, H-IPSE variants could be grouped into two clades of sequence variants. Even the most disparate clones share many homologous regions that allow targeting of all H-IPSE variants with genetic techniques. Two H-IPSE clones identical to the two principal variants predicted by both genome and transcriptome sequencing were produced by recombinant expression. These variants correspond to the predicted IPSE genes C_00050 and C_00244 (parasite.wormbase.org). Two variants, named H03 and H06, also were expressed in both bacterial and mammalian culture (the latter at 1-3 mg/L). These expressed proteins were analyzed by SDS and anti-His blot and produced bands of the expected size (FIG. 2c). M-IPSE protein was also produced in mammalian cells.

Intriguingly, the H03 and H06 H-IPSE homologs share only 63% and 68% identity with their S. mansoni counterpart, suggesting that these proteins may have evolved to suit each species' infectious niche and promote egg expulsion through distinct environments: the bladder and the liver/intestines. Despite this divergence, all H-IPSE variants retain several important features of M-IPSE, including a secretory signal, a nuclear localization sequence, cysteine residues required for both intra- and inter-chain disulfide bonds, and two N-linked Asn-X-Ser/Thr glycosylation consensus sequences (FIG. 2d).

Figure 3:
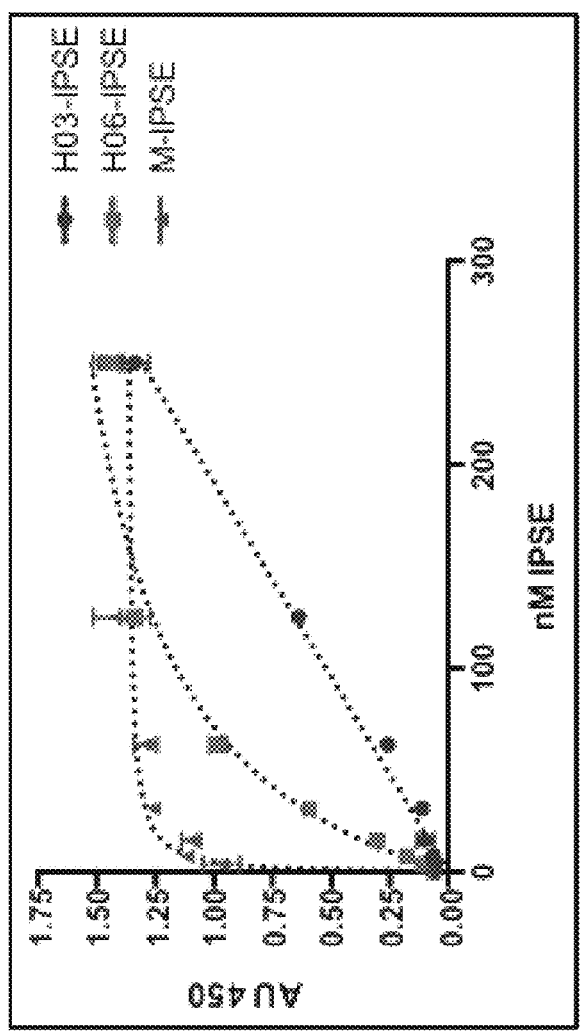
FIG. 3 shows that multiple forms of IPSE bind IgE. Full length human IgE was plated. Recombinant his-tagged IPSE (generated in mammalian HEK293-6E cells) was incubated at the indicated concentrations, and detected with a polyclonal anti-his-HRP conjugated antibody. All IPSE clones bound full length human IgE, with a range of affinities.
Figure 4:
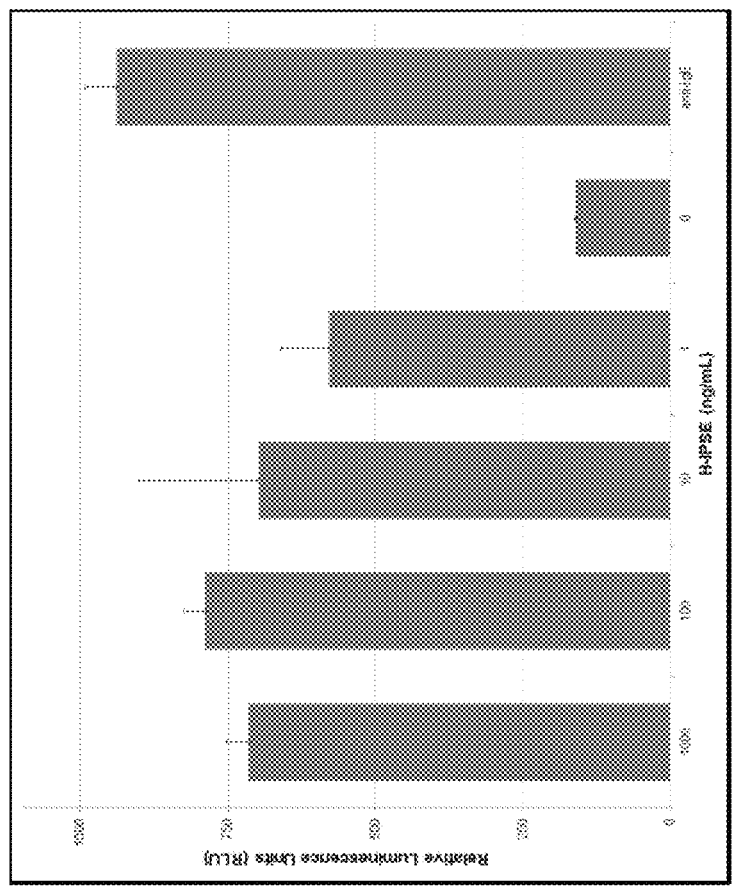
FIG. 4 shows the effect of H-IPSE on the IgE crosslinking reporter system RS-ATL8. RS-ATL8 are humanized rat basophilic leukemia cells reporting IgE-dependent activation by inducing Luciferase. Confluent RS-ATL8 cells were sensitized with (IgE-containing) human serum from an immunologically naive donor (not Schistosoma infected) overnight, washed twice and stimulated with the indicated amounts of H-IPSE. 4 hours later, cells were lysed and luciferase levels assessed using Promega OneGlo luciferase substrate, expressed as Relative Chemiluminescence Units (RLU)+/−standard deviation of triplicate repeats. Negative controls only contained cell culture medium, while positive controls contained an optimal amount (1 µg/mL) of goat-anti-human IgE. H-IPSE in all tested doses led to induction of luciferase, reflecting engagement of the IgE receptor. This activation was independent of IgE specificity.

Polyclonal rabbit IgG that recognizes recombinant and egg-derived IPSE was generated, and was used to confirm that S. haematobium eggs secrete H-IPSE (FIG. 2b). The immunoglobulin binding specificity of H03 and H06 H-IPSE was compared to that of M-IPSE. All three proteins bound to IgE, albeit at different affinities (FIG. 3). Consistent with H-IPSE's ability to bind to IgE, it was found that H-IPSE activates human IgE-bearing basophil-like reporter cells (FIG. 4). Thus, H-IPSE may bind to surface IgE on mast cells and basophils and trigger IL-4 secretion, analogous to M-IPSE.

Figure 5:
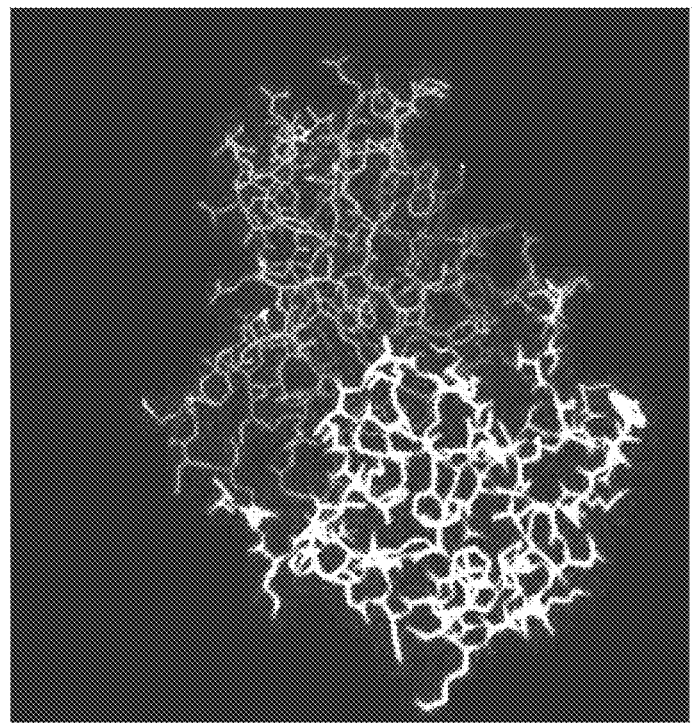
FIG. 5 shows models for IPSE-CCL2 binding using Autodock Vina. Top image shows predicted M-IPSE (green top structure)-CCL2 (pink bottom structure) binding, bottom image depicts predicted H-IPSE (green top structure)-CCL2 (pink bottom structure) binding. Note similarity between predicted M-IPSE and H-IPSE interactions with CCL2. The M-IPSE protein structure, as well as the CCL2 protein structure were downloaded from the RCSB Protein Data Bank (M-IPSE PDB ID: 4AKA, CCL2 PDB ID: 1DOK). The H-IPSE protein structure is a model generated via homology modeling using PHYRE2, with 78% of residues modeled at more than 90% confidence. The % similarity between M-IPSE and H-IPSE was at 60%. IPSE and CCL2 files, which were in PDB format were converted to PDBQT format using AutoDockTools-1.5.6. Autodock Vina was then successfully used to search for binding between IPSE and CCL2. The binding affinity for M-IPSE and CCL2 was at −14.1 kcal/mol, and that for H-IPSE and CCL2 was at −13.3. These values indicated strong binding between the two molecules. AutoDockTools-1.5.6 was then used to generate protein complex images.
Figure 5:
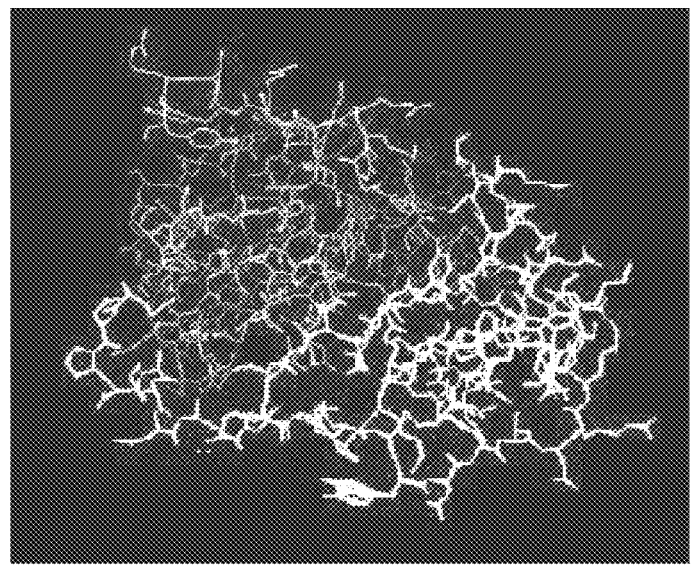

H-IPSE and M-IPSE may also have similarities with regards to chemokine binding. In silico data showed binding of H-IPSE to CCL2 in a similar fashion to how M-IPSE binds to CCL2 (FIG. 5).

Figure 6:
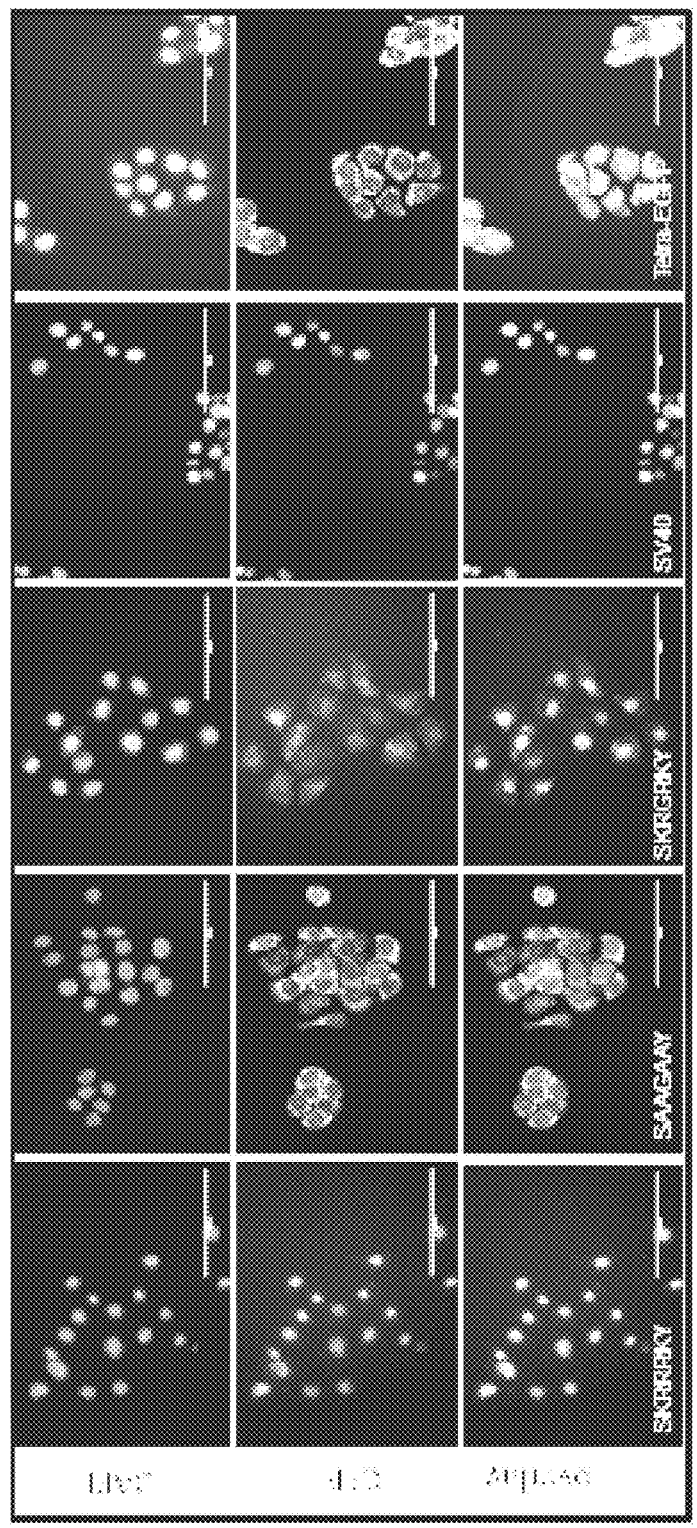
FIG. 6 shows the effect of multiple amino acid substitutions of the nuclear localization sequence of H-IPSE. The nucleotides encoding the H-IPSE nuclear localization sequence—SKRRRKY—(SEQ ID NO: 3) or —SKRGRKY—(SEQ ID NO:4) were inserted into the pTetra-EGFP construct. pTetra-EGFP encodes a tetrameric EGFP construct resulting in the expression of a fluorescent protein which due to its size (~100 kDa) is excluded from the nucleus of HTB-9 urothelial cells in the absence of a functional nuclear localization sequence [NLS] (Tetra-EGFP) or imported into the nucleus in the presence of a functional NLS (canonical SV40 NLS H-IPSE NLS SKRRRKY—(SEQ ID NO:3)—and SKRGRKY—(SEQ ID NO:4)). The presence of an uncharged G in the charged KRRRK (SEQ ID NO:5) core sequence of the NLS appeared to partially weaken its strength as a nuclear targeting signal, as documented by the mixed cytosolic/nuclear localization in contrast to the exclusive nuclear localization with the SKRRRKY—(SEQ ID NO: 3) sequence. Substitution of Lysine and Arginine with Alanine (SAAGAAY)—(SEQ ID NO: 6) resulted in a non-functional NLS which was no longer able to translocate the Tetra-EGFP protein into the nucleus. Nuclei were stained with DAPI and green fluorescence were measured in the GFP channel on an EVOS fl microscope 24 hours after transfection.

H-IPSE may also alter host biology through functional nuclear localization sequences (FIG. 6). This feature suggests that IPSE may be able to translocate to the host cell nucleus and induce changes in host gene expression. Accordingly, it has been shown that exogenously applied M-IPSE is able to translocate to the host cell nucleus and alter transcription of genes linked to cell adhesion, immune responses to wounding, and apoptosis (FIG. 1). H-IPSE translocates into urothelial cell nuclei, indicating that this molecule may also modulate transcription, akin to M-IPSE (FIG. 6). This activity is consistent with a potential role for H-IPSE in modulating urothelial biology.

Figure 7:
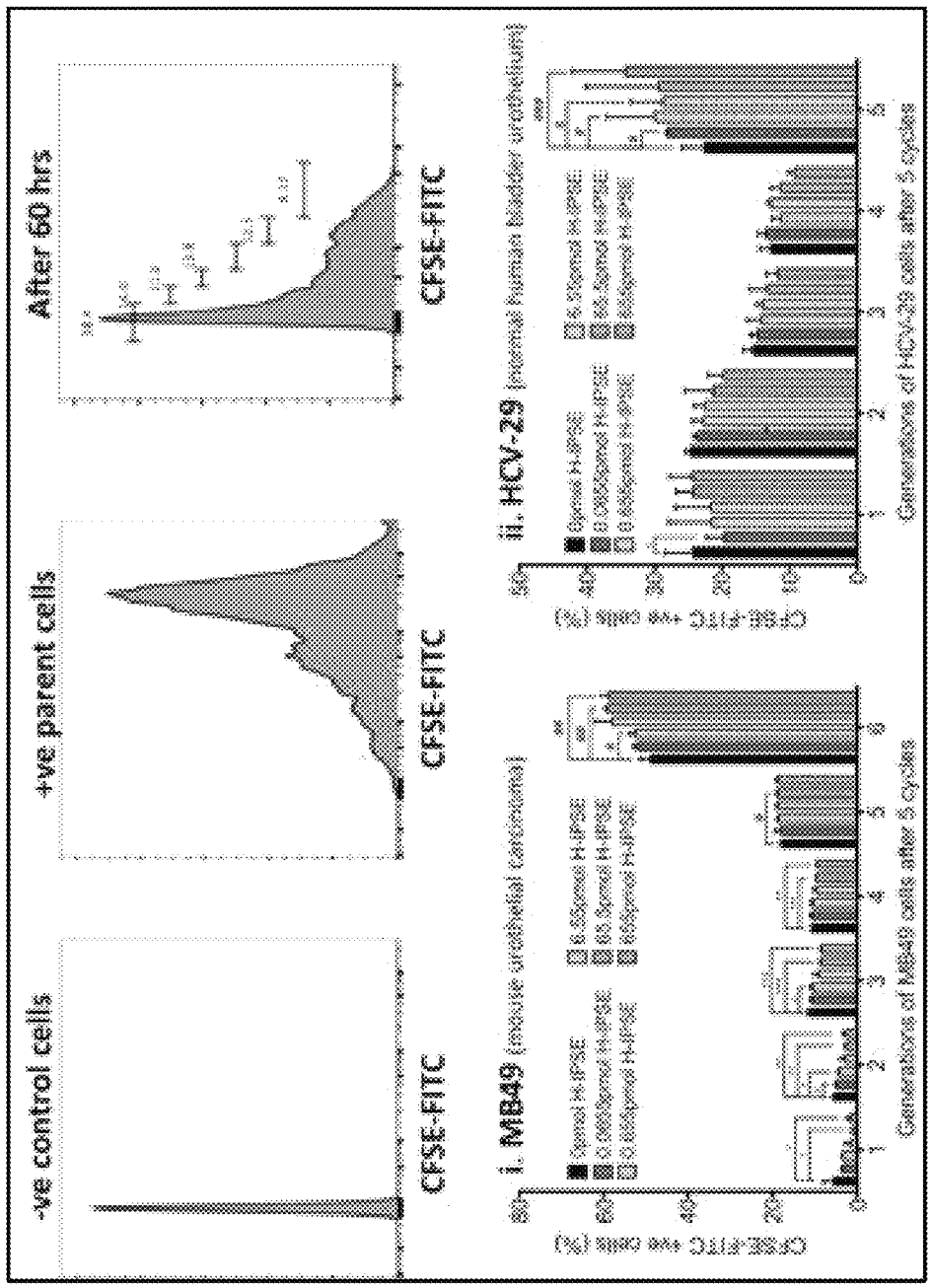
FIG. 7 shows that H-IPSE increased proliferation of urothelial cells. (A). A representative histogram showing unstained urothelial cells, parent cells after staining and before co-incubation with H-IPSE, and daughter generations of the cells after incubation with H-IPSE. The delineated peaks depict generations after each cell division. Quantitation of (B) MB49 mouse and (C) HCV29 human urothelial cell proliferation after incubation with increasing concentrations of H-IPSE. There was an H-IPSE concentration-dependent increase in cell proliferation as depicted by increased proportion of cells in later generations and concomitant decrease in proportions of cells in earlier generations.
Figure 8:
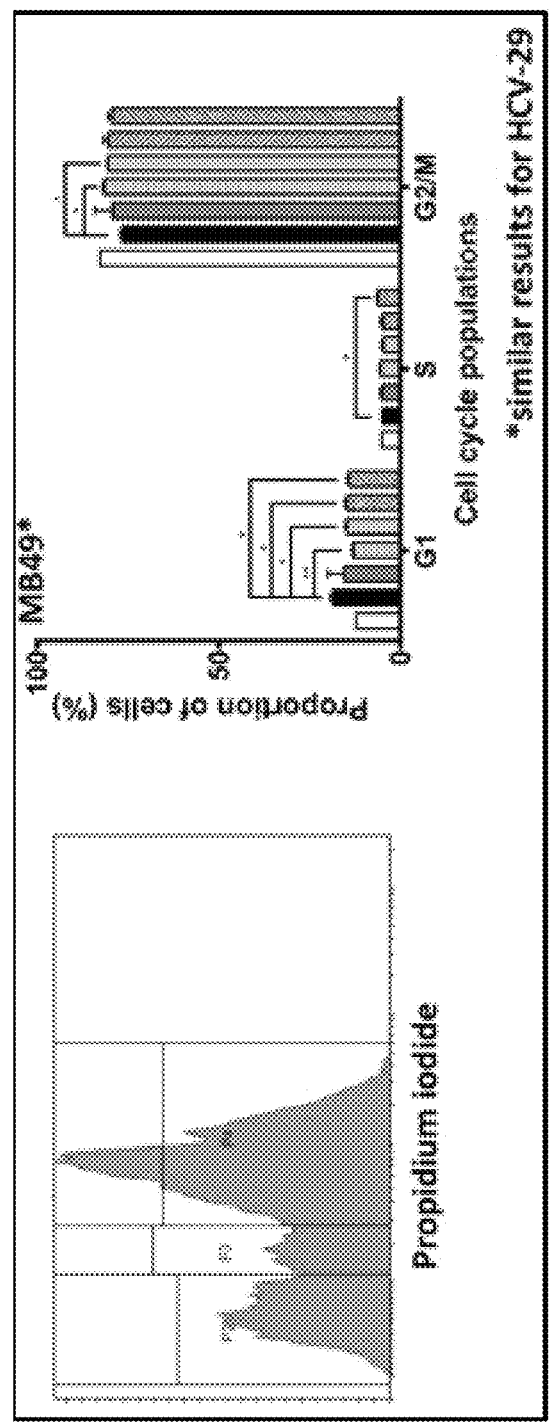
FIG. 8 shows that cell cycle analysis demonstrated that H-IPSE increases proliferation of urothelial cells. (A) After co-incubation with H-IPSE, cells were fixed and their DNA stained with propidium iodide and analyzed by flow cytometry. A representative histogram shows cells in the G1, S and G2/M phases of the cell cycle. Cells at G2/M phase were ready for mitosis and have about twice the amount of DNA as cells in G1 phase due to DNA replication, while cells in the S-phase had intermediate DNA content. (B) Quantification of the proportion of cells in different cell cycle phases. There was a significant decrease in the proportion of cells in the G1 phase and concomitant increase in the proportion of cells in the G2/M phase and the S phase.

Given the ability of H-IPSE to translocate into urothelial cells, the effects of H-IPSE on urothelial cell cycling and proliferation were characterized. CFSE-based flow cytometry assays were used to show that H06 H-IPSE enhanced proliferation of the MB49 mouse bladder cancer cell line and the HCV-29 human urothelial cell line (FIG. 7). Cell cycle analysis was employed to demonstrate that H06 H-IPSE increased the proportion of MB49 and HCV-29 cells in S phase and G2/M phase (FIG. 8). In short, these data demonstrate that H-IPSE is mitogenic for both mouse and human urothelial cells.

Further, in light of the broad host modulatory activities of H06 H-IPSE, we also tested this molecule for its analgesic properties in two models of bladder pain (ifosfamide-induced inflammatory pain and resiniferatoxin-induced neuropathic pain [capsaicin receptor-mediated]) and the carrageenan-induced footpad injection model of inflammatory pain).

Having established numerous pleiomorphic effects of H-IPSE on host biology, the effect of this molecule on the bladder, also was studied by testing the influence of H-IPSE on another form of interstitial cystitis, namely that caused by ifosfamide.

Figure 9:
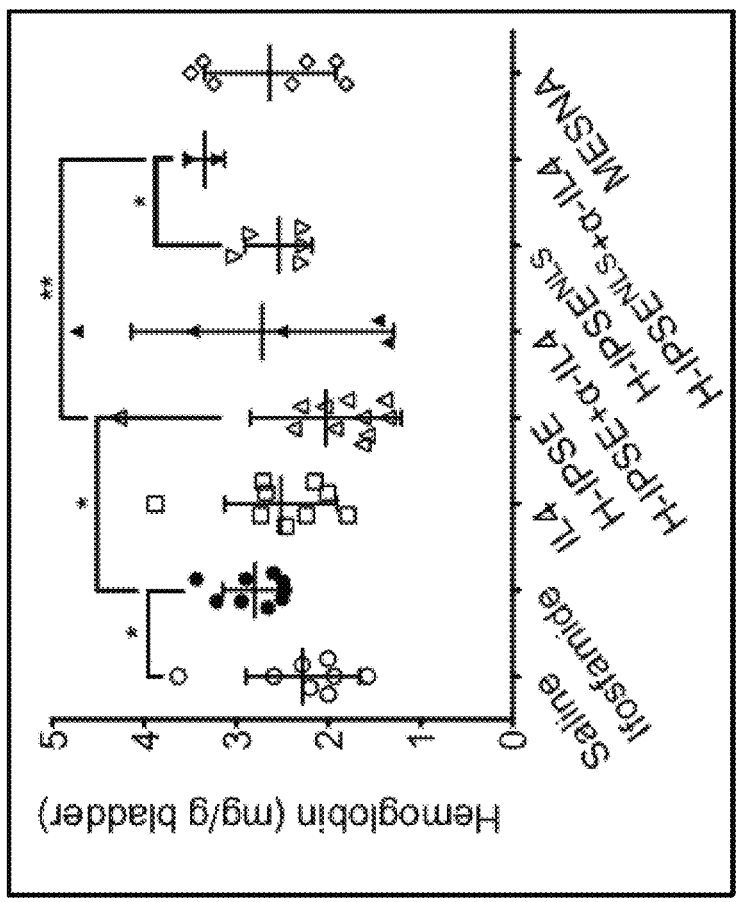
FIG. 9 shows that H-IPSE reduced ifosfamide-induced bladder hemorrhage. Mice were administered ifosfamide or saline, followed by recombinant IL-4, H-IPSE, H-IPSE with neutralizing anti-IL-4 antibody (α-IL4), nuclear localization sequence-mutant H-IPSE (NLS) with or without anti-IL-4 antibody, or Mesna. Animals were then sacrificed and their bladders excised and subjected to the Drabkin's test to measure tissue hemoglobin levels.
Figure 10:
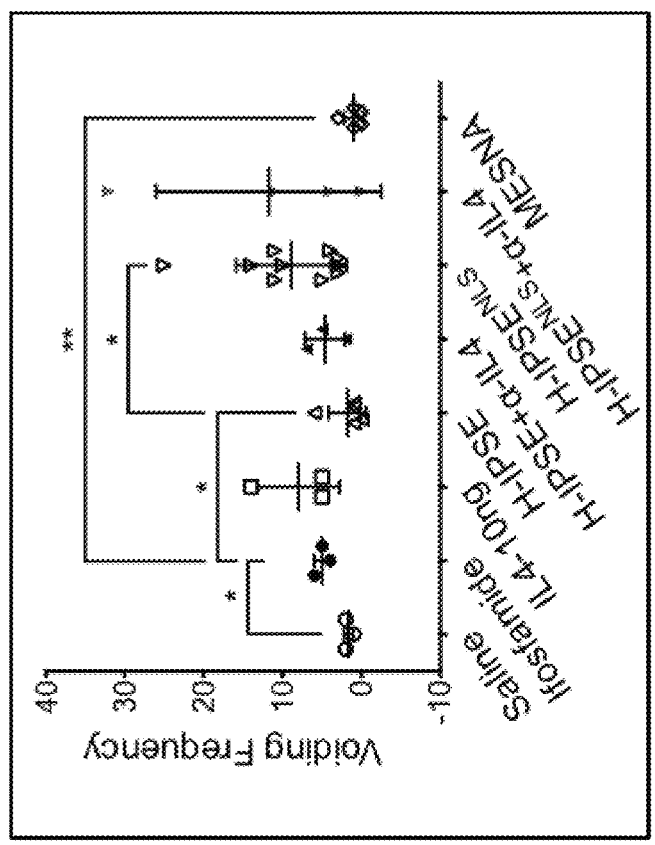
FIG. 10 shows that H-IPSE reduced ifosfamide-induced voiding frequency. Mice were administered ifosfamide or saline, followed by recombinant IL-4, H-IPSE, H-IPSE with neutralizing anti-IL-4 antibody (α-IL4), nuclear localization sequence-mutant H-IPSE (NLS) with or without anti-IL-4 antibody, or Mesna. Animals were then subjected to the voided spot on paper test to measure their voiding frequency over a six hour period.
Figure 11:
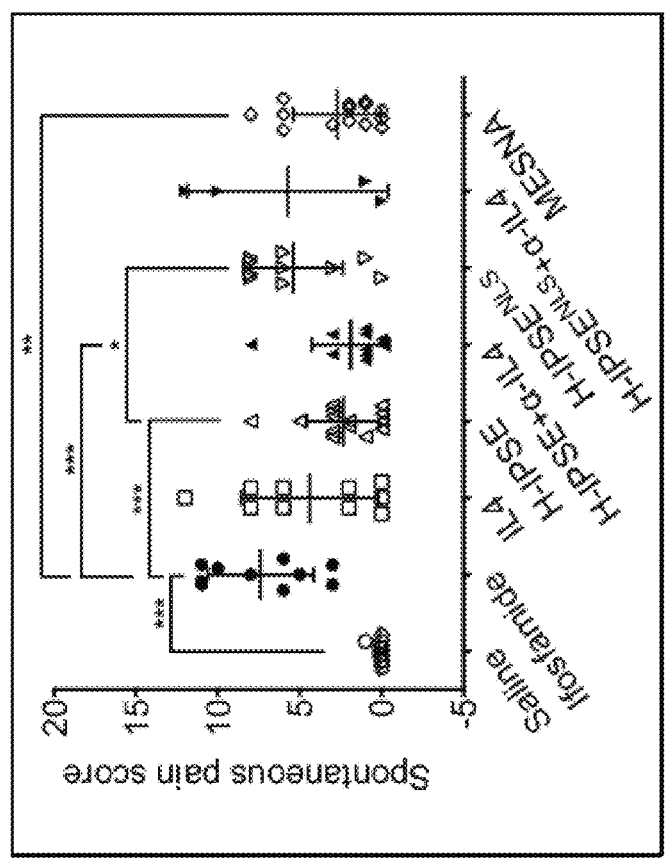
FIG. 11 shows H-IPSE reduced ifosfamide-induced, spontaneous pain. Mice were administered ifosfamide or saline, followed by recombinant IL-4, H-IPSE, H-IPSE with neutralizing anti-IL-4 antibody (α-IL4), nuclear localization sequence-mutant H-IPSE (NLS) with or without anti-IL-4 antibody, or Mesna. Animals were then placed individually in fresh cages with new bedding. After acclimatizing for 30 min, mice were evaluated and spontaneous pain scored (in a blinded fashion) by observing the mouse for one minute for any of these characteristics: Normal=0; Piloerection (ruffled fur)=1; Labored breathing=2; Ptosis (drooping of upper eyelid)=3; Licking of abdomen (not grooming)=4; Rounded back=5. The total score from this observation rating was used as an estimate of the overall pain score.

It was surprisingly found that a single intravenous dose of the naturally occurring H06 variant of H-IPSE was superior to Mesna and IL-4 in suppressing ifosfamide-induced bladder hemorrhage in mice (FIG. 9), and comparable to Mesna in dampening ifosfamide-induced urinary frequency and pain (FIGS. 10 and 11). Through use of neutralizing anti-IL-4 antibody and nuclear localization sequence mutants of H-IPSE, it was observed that H-IPSE's effects on ifosfamide-induced bladder hemorrhage and urinary frequency were both IL-4- and nuclear localization sequence-dependent. Conversely, H-IPSE's effects on ifosfamide-induced spontaneous pain behaviors were nuclear localization sequence-dependent, but did not depend on IL-4.

Figure 12:
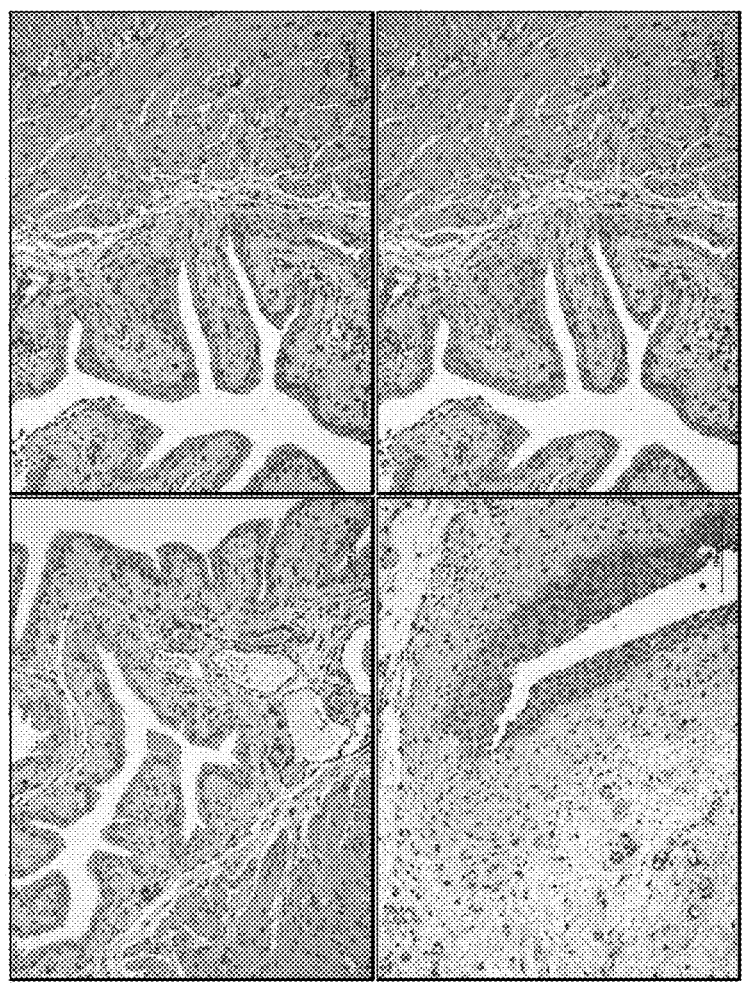
FIG. 12 shows that H-IPSE ameliorated histologically evident bladder damage caused by ifosfamide. Representative images from blinded histologic assessment of bladders from mice receiving: saline only (upper left), ifosfamide only (upper right), ifosfamide and recombinant IL-4 (lower left), and ifosfamide and H06 H-IPSE (lower right). Saline treated: normal urothelium. Ifosfamide: urothelial hyperplasia with reactive nuclear atypia and architectural disarray and segmental ulceration, severe edema with effacement of the submucosa, widespread vascular ectasia with occasional frank hemorrhage, and perivascular infiltrates. Ifosfamide and IL-4: urothelial hyperplasia with reactive nuclear atypia and architectural disarray, but without ulceration or erosion, severe edema with effacement of the submucosa, vascular ectasia and focal erythrocyte extravasation but no frank hemorrhage, with patchy perivascular infiltrates. Ifosfamide and IPSE: intact urothelium, normal nuclei, intact overall bladder architecture, lack of edema, absence of vascular ectasia, and no perivascular infiltrates.

The prophylactic properties of H-IPSE on ifosfamide-induced hemorrhagic cystitis has been histologically confirmed (FIG. 12).

Figure 13:
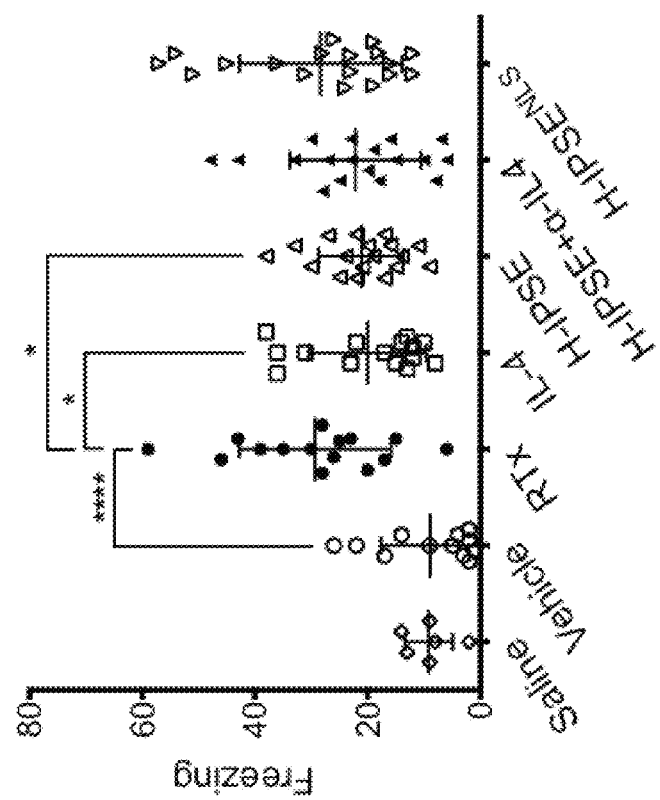
FIG. 13 shows intravesical resiniferatoxin-induced freezing behaviors were diminished by H06 H-IPSE in an IL-4- and nuclear localization sequence-dependent fashion. Female C57BL/6 mice (8-12 weeks of age) underwent no injection or injection with recombinant IL-4 ("IL-4"), H06 H-IPSE ("H-IPSE") with or without anti-IL-4 antibody ("α-IL4" signifies with antibody), or a nuclear localization sequence mutant of H06 H-IPSE ("H-IPSE$^{NLS}$"). Then, mice were placed under isoflurane general anesthesia and underwent urethral catheterization. 3 μM resiniferatoxin ("RTx") in 50 μL or vehicle control (10% ethanol and 10% DMSO in PBS) was instilled into the bladder via catheter for 1 minute. All mice that were administered IL-4 or H-IPSE variants also received resiniferatoxin. Catheters were removed and mice awakened and then video taped for behavioral analysis (performed in a blinded fashion). Freezing behaviors were scored every 5 seconds for each mouse over a 15 minute period.

Resiniferatoxin, the most potent known agonist for the capsaicin receptor, has been instilled intravesically into rats as a model of interstitial cystitis, visceral neuropathic pain and overactive bladder. Others have reported that administration of recombinant virus encoding the IL-4 gene results in decreases in resiniferatoxin-induced bladder and visceral pain. This led to testing of H-IPSE in resiniferatoxin-exposed mice. A single dose of H-IPSE was found to strongly inhibit pain behaviors induced by intravesical instillation of resiniferatoxin into the bladders of mice, and did so in an IL-4 and nuclear localization sequence-dependent fashion (FIG. 13). Thus, H-IPSE decreased bladder pain in two mechanistically different mouse models of interstitial cystitis and overactive bladder (ifosfamide and resiniferatoxin).

Figure 14:
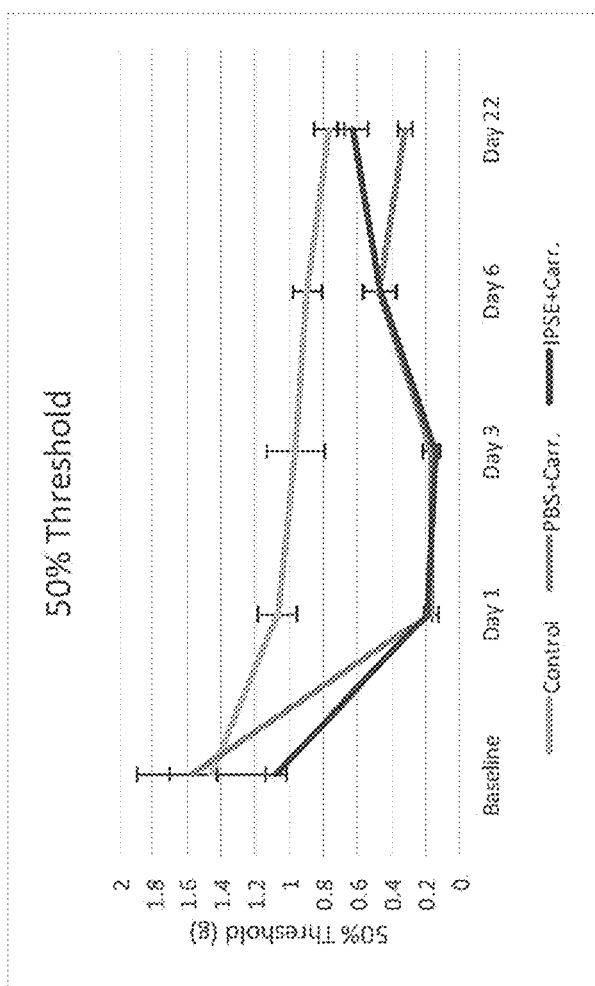
FIG. 14 shows that H06 H-IPSE reduced chronic carrageenan-induced inflammatory pain. Mice were tested for baseline pain using von Frey's filaments (blinded assessment). They then underwent intravenous injection with H06 H-IPSE, followed by footpad injection with carrageenan. Von Frey's filament testing was performed serially and in a blinded fashion through Day 22 post-carrageenan injection. 50% thresholds were calculated. Higher thresholds indicate less pain. At Day 22, mice injected with both H06 H-IPSE and carrageenan had pain scores similar to negative control mice, whereas mice injected only with carrageenan had persistent pain.

A single intravenous injection of H06 H-IPSE also reduced chronic inflammatory footpad pain induced by carrageenan injection (FIG. 14).

Definitions

As used herein, "interstitial cystitis", as defined by the International Continence Society, is "urinary urgency, with or without urge urinary incontinence, usually with frequency and nocturia".

As used herein, "pain", as used herein, is defined as any unpleasant sensory and emotional experience associated with actual or potential tissue damage, or described in terms of such damage.

As used herein, "overactive bladder", as defined by the International Continence Society, is ""urinary urgency, with or without urge urinary incontinence, usually with frequency and nocturia".

Neuropathic pain", as used herein, is defined as pain caused by a lesion or disease of a nerve or nerves.

"Inflammatory pain", as used herein, is defined as pain associated with a localized or generalized reaction that produces redness, warmth, and swelling as a result of infection, irritation, or injury.

"Prevention or treatment of pain", as used herein, is defined as successful decreases in pain as measured by instruments such as, but not limited to, the Wong-Baker Faces Pain Rating Scale, functional MRI, pupillometry, and changes in blood pressure, temperature, and pulse.

"IPSE protein" or "IPSE", as used herein, refers to Interleukin-4-Inducing Principle of *Schistosoma mansoni* Eggs (IPSE), and its derivatives, homologs, analogs, variants, mutants, and mimics. "IPSE" includes M-IPSE, H03 IPSE, H06 IPSE, any non-H03 IPSE homolog, non-H06 IPSE homolog, or any mutants of these homologs, or mimics. Any molecule with >50% amino acid sequence identity to M-IPSE will be defined as a homolog, variant, mutant, or mimic of IPSE.

"Treating interstitial cystitis", as used herein, is defined as successful reduction of any or all of the following signs and symptoms of interstitial cystitis: pain with urination, abdominal pain, urinary frequency, urinary incontinence, urinary urgency, small volume voids, urinary retention, sensation of incomplete voiding, nocturia, and urinary hesitancy.

In one aspect of the invention herein, a method is provided for intravenous injection of IPSE (1 mg/kg) to treat interstitial cystitis.

In another aspect of the invention herein, a method is provided for intravenous injection of IPSE (1 mg/kg) prior to exposure to painful stimuli.

In a further aspect of the invention herein, a method is provided for intravenous injection of IPSE (1 mg/kg) to treat overactive bladder.

In other preferred aspects, a different dose (higher or lower is given). In yet other preferred embodiments, IPSE is given subcutaneously at 1 mg/kg. In another embodiment, IPSE is given as one or more 1 mg/kg doses. In other preferred aspects, H03 H-IPSE, H06 H-IPSE, M-IPSE, or other H-IPSE homologs, variants, mutants or mimics of H03, H06, M-IPSE, or other H-IPSE homologs are administered.

Administration of IPSE

Methods are provided for treating or preventing pain, interstitial cystitis and/or overactive bladder by administration of at least one effective dose of an IPSE protein prior to, subsequent to, or contemporaneously with occurrence or establishment of pain, interstitial cystitis, and/or overactive bladder, or for treating pre-existing disease. The dose of IPSE can be, for example, about 1 mg/kg, but the skilled artisan will recognize that the dose administered can be higher or lower. The dosage may, for example, be .01.-10 mg/kg, for example 0.5, 1, 2, 3, 4, 5, 6, 7, 8, 9 or 10 mg/kg. The IPSE can be administered once or more than once, for example, 2, 3, 4, or 5 times.

The IPSE may be administered by any method known to be effective for administration of protein drugs; for example, administration may be via intravenous or subcutaneous injection. Multiple dosages may be administered at the same or different dosages. For example, an initial dose may be higher or lower than subsequent doses. In another embodiment, IPSE would be given as multiple 1 mg/kg doses. Each dose can be administered before and/or after occurrence or establishment of pain, interstitial cystitis and/or overactive bladder, or exclusively before exposure, or only following exposure.

Therapeutic Formulation and Administration

Pharmaceutical compositions comprising the IPSE protein are provided, where the protein is formulated with one or more suitable carriers, excipients, diluents and/or other agents that provide improved delivery, stability, reduced side-effects, and the like. Examples of suitable formulations can be found in, for example, Remington's Pharmaceutical Sciences, (Mack Publishing Company, Easton, Pa.). These formulations can include, for example, powders, pastes, ointments, jellies, waxes, oils, lipids, liposomal formulations, lipid containing vesicles, oil-in-water and water-in-oil emulsions, and other emulsions and suspended formulations. Suitable components for such formulations are well known in the art. See, for example, Powell et al., "Compendium of excipients for parenteral formulations" J. Pharm. Sci. Technol. 52:238-311 (1998).

The dose of IPSE administered to a subject, such as a human patient, may vary depending upon the age and the size of the patient, conditions, route of administration, and the like. The preferred dose is typically calculated according to body weight or body surface area. When an IPSE protein is used for treating or preventing pain, interstitial cystitis and/or overactive bladder in an adult patient, it may be advantageous to intravenously administer the protein normally at a single dose of about 0.1 to about 20 mg/kg body weight, for example about 0.2 to about 7, about 0.3 to about 5, or about 0.5 to about 3 mg/kg body weight. Depending on the severity of the condition, the frequency and the duration of the treatment can be adjusted. Effective dosages and schedules for administering IPSE protein or pharmaceutical compositions containing IPSE protein may be determined empirically; for example, patient progress can be monitored by periodic assessment, and the dose adjusted accordingly. Moreover, interspecies scaling of dosages can be performed using well-known methods in the art (e.g., Mordenti et al., Pharmaceut. Res. 8:1351 (1991).

Various delivery systems are known and can be used to administer the IPSE protein or pharmaceutical composition, e.g., encapsulation in liposomes, microparticles, microcapsules, and recombinant cells capable of expressing the protein. Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition as described herein can be delivered subcutaneously or intravenously with a standard needle and syringe. In addition, with respect to subcutaneous delivery, a pen delivery device readily has applications in delivering the pharmaceutical composition. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded. Suitable reusable pen and autoinjector delivery devices are well known in the art.

In certain situations, the pharmaceutical composition can be delivered in a controlled release system. For example, a pump may be used, or controlled release polymeric materials can be used; see, Medical Applications of Controlled Release, Langer and Wise (eds.), 1974, CRC Pres., Boca Raton, Fla. In another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed by Langer, Science 249:1527-1533 (1990).

Injectable preparations may include dosage forms for intravenous, subcutaneous, intracutaneous and intramuscular injections, drip infusions, etc. These injectable preparations may be prepared by methods that are well known in the art. For example, the injectable preparations may be prepared by dissolving, suspending or emulsifying the protein in a sterile aqueous medium or an oily medium conventionally used for injections. Suitable aqueous media for injections include, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], and the like. For an oily medium, suitable oils include, for example, sesame oil, soybean oil, etc., which may be used in combination with a solubilizing agent such as benzyl benzoate, benzyl alcohol, and the like. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid protein contained is generally about 5 to about 500 mg per dosage form in a unit dose; especially in the form of injection, it is preferred that the protein is contained in about 5 to about 100 mg and in about 10 to about 250 mg for the other dosage forms.

What is claimed is:

1. A method of treating overactive bladder in a subject comprising administering to said subject a therapeutically effective dose of an Interleukin-4-Inducing Principle of *Schistosoma mansoni* eggs (IPSE) protein.

2. The method of claim 1, wherein said IPSE protein is selected from the group consisting of: H03 H-IPSE, H06 H-IPSE, and M-IPSE.

3. The method according to claim 2, wherein said IPSE protein is H03 H-IPSE.

4. The method according to claim 2, wherein said IPSE protein is H06 H-IPSE.

5. The method according to claim 2, wherein said IPSE protein is M-IPSE.

6. The method according to claim 1, wherein said therapeutically effective dose is administered prior to and/or after development of overactive bladder.

7. The method according to claim 1, further comprising administering one or more additional effective doses of an IPSE protein.

8. The method according to claim 1, wherein administration of the therapeutically effective dose is performed intravenously, subcutaneously, transdermally, rectally, or orally, or is inhaled.

9. The method according to claim 1, wherein the therapeutically effective dose is delivered to the subject as a single administration, a serial administration, or a continuous administration.

10. The method according to claim 1, wherein the therapeutically effective dose is delivered as a serial administration.

11. The method according to claim 10 wherein the therapeutically effective dose delivered as a serial administration is administered at least every 5 minutes or is administered at most once weekly.

12. The method according to claim 1, wherein the therapeutically effective dose is delivered as a continuous administration.

13. The method according to claim 12, wherein the therapeutically effective dose delivered as a continuous administration is administered over the course of one minute or is administered over the course of four hours.

14. The method according to claim 1, wherein said IPSE protein is administered in a dosage of at least 1 mg/kg.

* * * * *